United States Patent
Lychock, III

(10) Patent No.: US 11,020,267 B2
(45) Date of Patent: Jun. 1, 2021

(54) ENERGY SOURCE HOLDER SYSTEM

(71) Applicant: George Robert Lychock, III, Quincy, MA (US)

(72) Inventor: George Robert Lychock, III, Quincy, MA (US)

(*) Notice: Subject to any disclaimer, the term of this patent is extended or adjusted under 35 U.S.C. 154(b) by 109 days.

(21) Appl. No.: 16/273,153

(22) Filed: Feb. 12, 2019

(65) Prior Publication Data
US 2020/0253779 A1    Aug. 13, 2020

(51) Int. Cl.
*A61F 7/02* (2006.01)
*A41D 13/005* (2006.01)

(52) U.S. Cl.
CPC ............. *A61F 7/02* (2013.01); *A41D 13/005* (2013.01); *A61F 2007/023* (2013.01)

(58) Field of Classification Search
CPC ............... A61F 2007/0225; A61F 7/02; A61F 2007/0228; A61F 2007/0231; A61F 2007/0009; A61F 2007/0011; A61F 2007/001; A61F 2007/023; A41D 13/005
See application file for complete search history.

(56) References Cited

U.S. PATENT DOCUMENTS

| | | | |
|---|---|---|---|
| 5,074,300 A * | 12/1991 | Murphy | A61F 7/08 383/107 |
| 2002/0052569 A1* | 5/2002 | Horning | A61F 7/10 602/41 |
| 2005/0222655 A1* | 10/2005 | Boyd | A61F 7/08 607/114 |
| 2005/0240251 A1* | 10/2005 | Smith | A61F 7/103 607/114 |
| 2013/0012760 A1* | 1/2013 | Tripolsky | A61F 5/028 600/15 |
| 2016/0199222 A1* | 7/2016 | Mullen, Sr. | A61F 7/02 607/112 |
| 2019/0151157 A1* | 5/2019 | Herder | A61F 13/00063 |

* cited by examiner

*Primary Examiner* — Daniel J Colilla

(57) ABSTRACT

In accordance with one embodiment, as originally conceived, a holder system is given that comprises a main body with a compartment for storing an energy source, such as a heating or cooling pack, and a method for securing the source within the compartment. The main body at one end contains a bottom cord with 2 loops, one at each end. A top drawcord is attached at the opposite end of the main body. Each end of the top drawcord wraps around a host object and is inserted into one of the bottom cord loops. Cord stops attached to each end of the top drawcord cinch the main body, with energy source, around a host.

1 Claim, 4 Drawing Sheets

ENERGY SOURCE HOLDER SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Field of the Invention

Prior heating or cooling garments are generally comprised of a full garment outfitted with a compartment(s) to hold energy sources such as chemically-activated or air-activated heating or cooling packets. The gainful effect is for a user to experience a warmer or cooler environment than normally given by the garment itself. Prior heating and cooling garments limit the user to the application and placement of the heating or cooling effect. Certain heating or cooling garments may be of a fashion that is not desirable to the end user. By incorporating the heat or cold source directly into the end user garment, prior art forces the end user to wear a garment that is not desired or not fashionably complementary to the other garments the user might be wearing. Placement of the actual heating or cooling source is governed by the location of the compartments holding the source in the prior art and how the garment falls on any one user's body. Prior art may not be suitable for, or the effect is inconsistent for, persons of different size and weight. The prior art may only be appropriate for humans but not others, say a pet or nonliving thing.

As a result there exists a need in the art for a lightweight, easily reusable and adjustable energy source holder that acts as an attachment to existing garments allowing for multiple applications, both human and non-human, that is not dependent on the size and shape of the user or subject, and that allows for many aesthetically pleasing and pricing variations. Energy sources come in a variety of types: cold generating, heat generating, magnetic therapy, or electronic pulse (massage) generating, as examples. A complimentary, but mutually exclusive answer to the prior art would be a system that can more universally apply the multiple variations of energy source effects to a larger number of applications and positions.

Description of the Related Art

Prior art for heating or heated garments such as U.S. Pat. No. 5,086,629 (1992) to Carroll M. Dibrell, U.S. Pat. No. 7,251,837 (2007) to Charles D. Horton, U.S. Pat. No. 7,069,598B1 (2006) to Brian Walsh, U.S. Pat. No. 8,092,406 (2012) to Robert M. Gorsen, or US20110214222A1 (2011) to Lawrence Knight and Dee Ann Knight, exhibit the advantage of applying the energy source affects to a user's body by providing predefined pockets or other holding mechanisms on a finished garment designed to be worn or applied 'as is', forcing the user, while gaining the effects of the energy source, to wear or apply a garment that is larger, bulkier, less positionally flexible, or less aesthetically pleasing than what the user may normally or preferably wear.

U.S. Pat. No. 5,086,629 'Scarf For Transferring Heat From Or To Body Areas Of The Wearer', in one example, provides several pockets for holding an energy source on a prefabricated scarf. The scarf provides limited fashion-centric flexibility but is deficient in its ability to position the energy sources at more desirable locations dependent on the a user's preference. Although not a main garment, more of an accessory, the prior art is still more bulky and limited as proposed in the present disclosure.

U.S. Pat. No. 7,069,598B1 'Necked Garment Having Built-In Receptacle For Air Activated Heater' is a complete solution for providing a heating effect via an air activated packet to a user's body Designed to be used independently, the product is limited in its ability to satisfy a user's desire for more complimentary fashion to what the user is accustomed to.

U.S. Pat. No. 7,251,837 'Hand Warming Method And Apparatus' is a medical utility garment specifically designed to apply a heat source to a hand. The prior art cannot be applied in any other obvious manner to the user's body. Continuing with prior art geared towards medical applications, U.S. Pat. No. 8,092,406 'Therapeutic Belt' is designed to apply various therapeutic components to a user's body but does not exhibit the flexibility to be attached to an existing garment already owned, worn, or desired by the user. U.S. Pat. No. 8,771,331 'Wrap For Applying Thermal Therapy To A Body Part' provides for applying cooling or thermal effects to a variety of body parts or areas, but is not designed to be attached to an existing garment for use as a more fashion oriented solution for applying an energy source effect in a more casual scenario. A casual scenario may include recreational events such as skiing, sporting event attendance, or commuting to work.

U.S. Pat. No. 5,605,144A 'Heating Garment With Pouch For Accommodating Inserted Heating Packets', US 2011/0041229 A1 'Hot Pox Outdoor Gear', and US20130061370A1 'Neck Scarf For Cooling Or Warming The User' all propose art that would provide heating packet pockets at various predefined positions on numerous finished garments such as gloves, sweaters, pants, etc. The inability of the user to position the energy sources at the most desired areas of the body in addition to its bulkiness, and limitation fashionably, is tantamount to expressing the void in existing art and the need for a more flexible, lightweight solution demonstrated by the present disclosure;

an apparatus that allows a user to attach an energy source in an adjustable position to an existing host garment.

Summarizing, resultant disadvantages of prior art are as follows:
(a) The host garment is a complete piece of clothing such as a coat, scarf, or pants that users are expected to use in its entirety to take advantage of the energy source effect.
(b) The larger size, complexity, or specificity of prior art restricts or prohibits the ability to apply the energy source effect at a user's preferred location.
(c) The larger size and complexity, or specificity, restricts the ability to offer a wider range of textile and fabric types.
(d) The size and bulkiness takes away from the energy source effectiveness and versatility.
(e) They are made for a single purpose, eg. A warming scarf (See HotMocs, Venture Heat Battery Heated Scarf); a heated coat, warming socks, cooling towel, Hot Hands Hand/Back Warming Belt or warming hat. These products do not allow the user to apply the heating or cooling effect in more than one way.
(f) Prior art garments are not easily stored, eg. in a purse or knapsack, due to the size and specificity of their application.
(g) prior art does not necessarily promote the use of, suggest the use of, or provide for the use of, alternative energy sources such as generating or emitting sources such as magnetic, electronic, or other energy sources.

BRIEF SUMMARY OF THE INVENTION

The embodiment, as presented in the disclosure, offers a more flexible positioning of the energy source as compared to prior art prefabricated garments that are retrofitted to accept a heating source by including pockets directly incorporated into the garment such as the Techniche ThermaFur Heating Scarf, ASIN: B009GJ9P52, Crown House, 30 Commerce Road, Brentford, TW8 8LE. or HotMocs™ Fleece Scarf, HotMocs, 15535 W. Hardy, Suite 102, Houston, Tex., 77060. 281-448.4860. hotmocs dot com. In these examples placement of the actual heating or cooling source is governed by the location of the compartments in the prior art used to hold the source and how the garment falls on any user's body. The embodiment can be configured and constructed to address a plurality of applications where the need exists for an adjustable holder mechanism with the ability to hold several types of energy generating sources at a multitude of positions based on the user's or receiver's preference.

BRIEF DESCRIPTION OF DRAWINGS

The accompanying drawings, which are included to provide a further understanding of the disclosure, are incorporated in and constitute a part of this specification, illustrate embodiments of the disclosure, and together with the detailed description, serve to explain the principles of the disclosure. No attempt is made to show structural details of the disclosure in more detail than may be necessary for a fundamental understanding of the disclosure and the various ways in which it may be practiced. In the drawings.

DRAWINGS—REFERENCE NUMERALS

Figure 1:
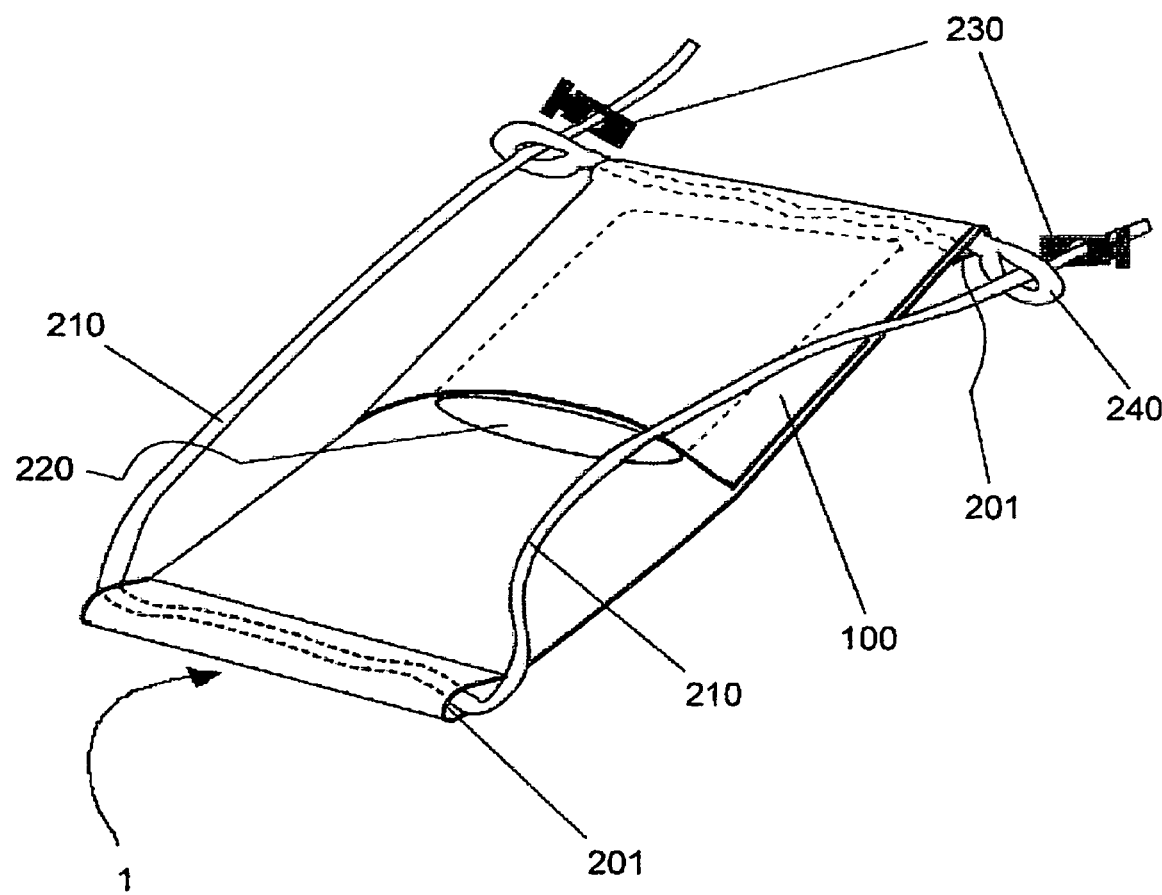
FIG. 1 shows an energy source holder system, with a holder body, a holder pocket, and attachment method (tethered), used to secure an energy generating source to a target object in accordance with one embodiment.

1 holder body
2 holder system
230 cord stop
240 bottom cord with loops
10 host object
10a host object
100 holder pocket
201 channel
210 top drawcord
220 energy generating source
220a energy generating source

DETAILED DESCRIPTION OF THE INVENTION

The embodiments of the disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein Descriptions of well-known components may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

In accordance with one embodiment of the energy source holder system FIG. 1 shows an inside view of a holder body 1 in combination with a holder pocket 100. The holder pocket is used to secure an energy generating source 220, such as a heat or cold source, to said holder body. Holder body 1 is constructed with a channel 201 at the top and bottom. A top drawcord 210 and a bottom cord with loops 240 are inserted into the top and bottom channels respectively, providing an attachment method for securing said holder body in combination with said holder pocket to a target object. The ends of the top drawcord weave thru the loops in the bottom cord. A cord stop 230 is attached to both ends of the top drawcord.

Continuing to reference FIG. 1, energy generating source 220 is installed into the holder pocket 100. The top drawcord 210 is wrapped around one side of a host object such as, but not limited to, a scarf, holding said holder body with holder pocket securing said energy generating source against said host object. Both ends of the top drawcord are inserted through the loops of bottom cord 240. The cord stops 230 are installed at each end of the top drawcord and adjusted by pulling the top drawcord further through the loops and cinching the cord stop up towards the loops of the bottom cord.

Holder body 1, and subsequently holder pocket 100, can be created from a pliable material such as fabric like cotton or wool, plastic, leather, or any natural or synthetic that allows for the flexibility needed to create an effect holding mechanism for an energy generating source such as a heat or cold generating source.

Energy generating source 220 might be an air-activated chemically based product such as the HotHand Hand Warmer, ASIN: BOOPX20LOO, available from Hot Hands, KOBAYASHI Consumer Products, LLC. Dalton, Ga., or any other method or device that creates or projects a physical effect such as a cold pack, microwavable sources, magnetic or electronic sources of energy.

Top drawcord 210, and subsequently bottom cord with loops 240, might be fabricated from parachute cord or any rope type of textile that can satisfy the needs of the present embodiment.

Cord stop 230 might be a feed and clinch product such as Dritz® Cord Stops, GTIN 00072879116663, available from Dritz, Spartanburg, S.C. USA.

Figure 2:
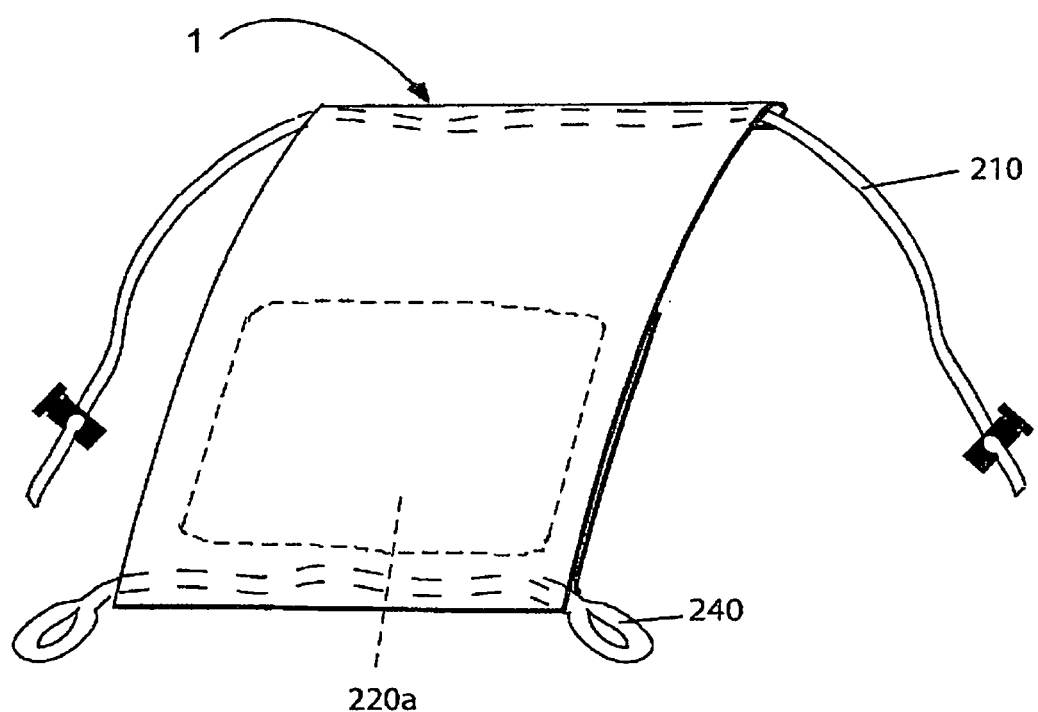
FIG. 2 shows an energy source holder system, with a holder body, a holder pocket, and attachment method (untethered), used to secure an energy generating source to a target object in accordance with one embodiment.

FIG. 2 shows an example of a reverse view of the embodiment as previously described in FIG. 1. Holder body 1 is fitted with bottom cord 240 and top drawcord 210, both of which are inserted into the top and bottom cord channels as previously described in FIG. 1. The example also depicts approximate position of an energy generating source 220a within the holder pocket.

Figure 3:
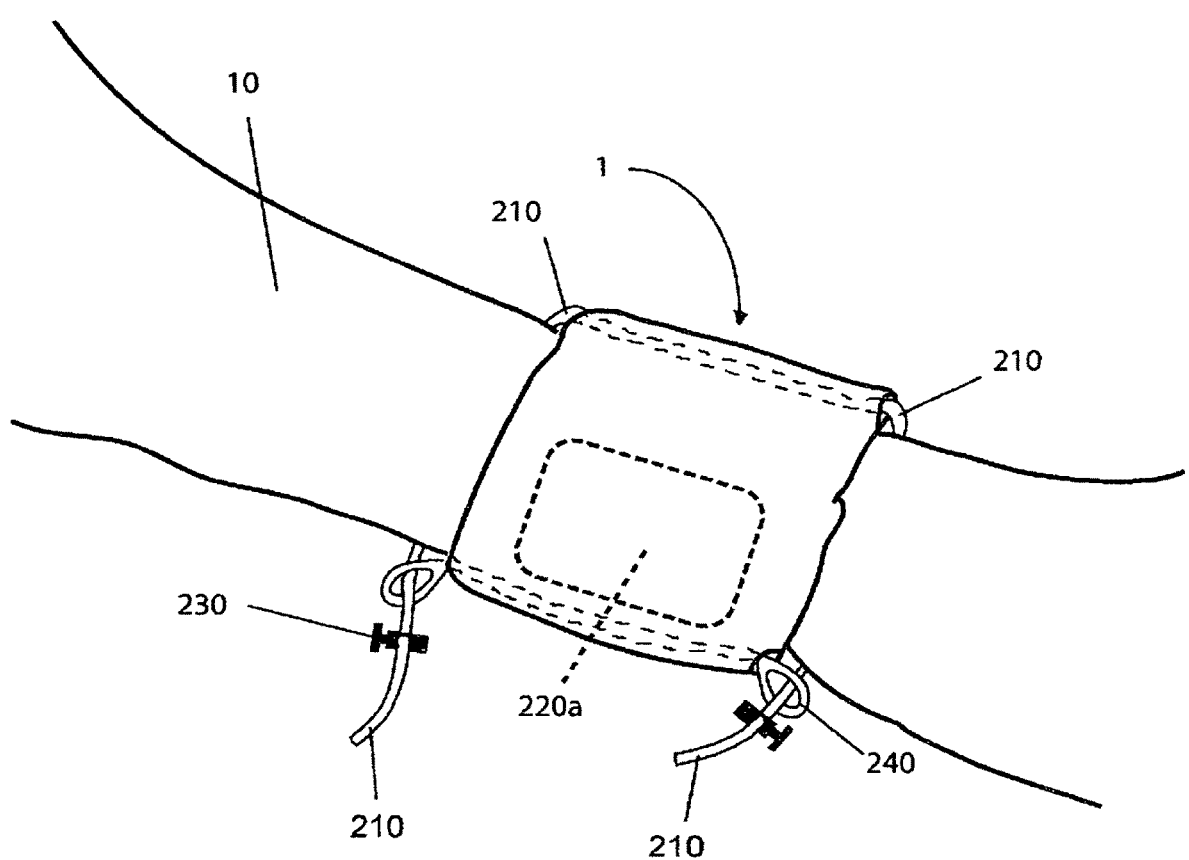
FIG. 3 shows an energy source holder system, with a holder body, a holder pocket, and attachment method (tethered), secured to a target object in accordance with one embodiment.

FIG. 3 shows the embodiment as previously described in FIG. 1 with holder body 1 secured around a host object 10. Holder body 1 is fitted with the top drawcord 210 and the bottom cord with loops 240 inserted through top and bottom channels respectively, as previously described in FIG. 1. Both ends of the top drawcord wrap around the backside of the host object securing the holder body around the front side of said host object. Each end of the top drawcord is weaved through each loop of the bottom cord with loops where the cord stop 230 is installed at both ends of said top drawcord to adjust the level of tightness of the embodiment around the host object Energy generating source 220a is shown inserted in holder body 1. Host object 10 can be one of many items, including a scarf, and can be selectively positioned anywhere along many target host objects.

Figure 4:
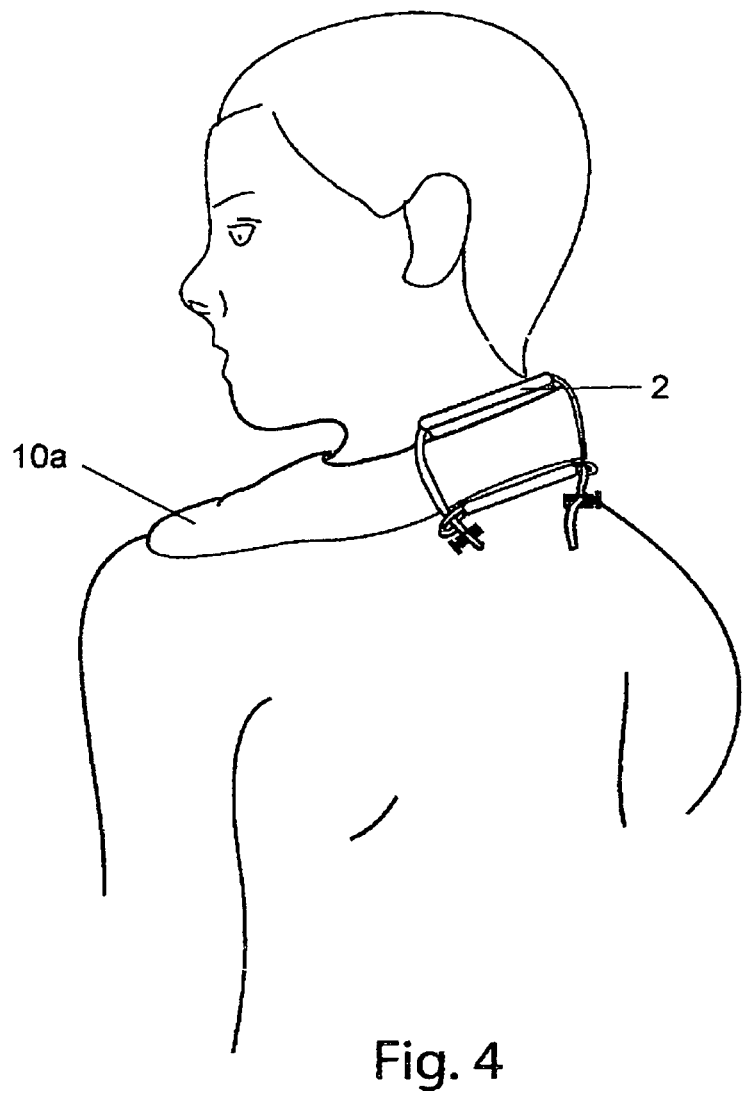
FIG. 4 shows an energy source holder system, with a holder body, a holder pocket, and attachment method (tethered), secured to a target object applied to a host in accordance with one embodiment.

FIG. 4 shows the embodiment as previously described in FIG. 1 with a holder system 2 attached to a host object 10a wrapped around a target, in this case, an individual. While not explicitly depicted, the energy generating source is installed in the holder system positioning it against the body of the individual depicted.

What is claimed is:

1. A holder body comprising:
    an adjustable fastener configured to be attached to a host object that is subsequently applied to a target object desired to be the recipient of the effect of an energy source;
    an energy source;
    a means for receiving and then securing said energy source to the holder body,
    wherein said adjustable fastener is substantially flexible enough to secure the holder body, in connection with the energy source, at an arbitrary position to various host objects, and
    wherein said adjustable fastener consists of:
    a bottom cord with a loop at each of a first end and a second end, said bottom cord being attached to a first end of the holder body;
    a top drawcord attached to the holder body at a second end of the holder body opposite the first end, wherein each end of said drawcord is configured to be inserted through a respective one of said bottom cord loops; and
    a cord stop applied to each end of the top drawcord thereby allowing the top drawcord to be cinched, effectively pulling the energy source holder system tightly around the host object.

* * * * *